United States Patent [19]

Rajadhyaksha

[11] 3,989,815

[45] Nov. 2, 1976

[54] NOVEL N-BIS-AZACYCLOPENTAN-2-ONYL ALKANES

[75] Inventor: Vithal Jagannath Rajadhyaksha, Mission Viejo, Calif.

[73] Assignee: Nelson Research & Development Company, Irvine, Calif.

[22] Filed: June 19, 1975

[21] Appl. No.: 588,248

[52] U.S. Cl. ................................. 424/60; 424/59; 424/88; 424/181; 424/238; 424/251; 424/274
[51] Int. Cl.$^2$ ..................... A61K 7/44; A61K 31/40
[58] Field of Search ............................. 424/274, 60

[56] References Cited
UNITED STATES PATENTS

| | | | |
|---|---|---|---|
| 3,085,931 | 4/1963 | Darlington | 424/274 |
| 3,551,554 | 12/1970 | Herschler | 424/274 |
| 3,891,757 | 6/1975 | Higuchi | 424/274 |

OTHER PUBLICATIONS

Chemical Abstracts, 73:102083 d, (1970).

*Primary Examiner*—Norman A. Drezin
*Attorney, Agent, or Firm*—Martin A. Voet

[57] ABSTRACT

There is disclosed an improved method for topically administering a physiologically active agent to a human or animal by dissolving an effective amount of the agent in a carrier containing suitable amounts of N-bis-azacyclopentan-2-onyl alkanes, as defined herein, and contacting the skin or other membranes of the human or animal with the resulting composition, whereby penetration of the skin or membranes is enhanced.

11 Claims, No Drawings

NOVEL N-BIS-AZACYCLOPENTAN-2-ONYL ALKANES

BACKGROUND OF THE INVENTION

Many physiologically active agents are best applied topically to obtain desirable results. Topical application, as contrasted to systemic application, largely avoids side effects of the agents and permits high local concentrations of the agents.

The greatest problem in applying physiologically active agents topically is that the skin is such an effective barrier to penetration. The epidermis of the skin has an exterior layer of dead cells called the stratum corneum which is tightly compacted and oily and which provides an effective barrier against gaseous, solid or liquid chemical agents, whether used alone or in water or oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penentrate the stratum corneum prevents their effective use to treat such conditions as inflamation, acne, psoriasis, herpes simplex, eczema, infections due to fungus, virus or other microorganisms, or other disorders or conditions of the skin or mucuous membranes, or of conditions beneath the exterior surface of the skin or mucous membranes. The stratum corneum also prevents the skin from absorbing and retaining cosmetic-type materials such as sunscreens, perfumes, mosquito repellants and the like.

Physiologically active agents may be applied to locally affected parts of the body through the vehicle system described herein. Vehicles such as USP cold cream, ethanol and various ointments, oils, solvents, and emulsions have been used heretofore to apply physiologically active ingredients locally. Most such vehicles are not effective to carry significant amounts of physiologically active agents through the skin. One such vehicle is dimethyl sulfoxide, which is described in U.S. Pat. No. 3,551,554. In this description, the term "animal" includes human beings as well as other forms of animal life, and especially domesticated animals and pets.

SUMMARY OF THE INVENTION

This invention is a method for carrying physiologically active agents through body membranes such as skin and for retaining these agents in body tissues. The invention also relates to compositions for use in the method. More specifically, the invention relates to a method for topically adminstering a physiologically active agent to a human or animal comprising administering topically to a human or animal an effective amount of a composition containing the agent and an effective, non-toxic amount of a compound having the structural formula

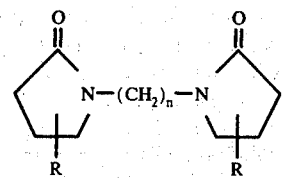

wherein R is H or a lower alkyl group having 1–4 carbon atoms and n is a positive integer from 1–18 and preferably 3–10. In a preferred embodiment, R is H and n is 3.

The invention also relates to novel compounds having the foregoing structural formula.

It has been found that the physiologically active agents are carried through body membranes by the claimed vehicles and are retained in body tissues.

DETAILED DESCRIPTION OF THE INVENTION

Referring more particularly to the above structural formula, the carbon chain formed between the azacyclopentan-2-one rings may be straight or branched. n is a positive integer from 1–18 and preferably from 3–10. R is H or an alkyl group having 1–4 carbon atoms.

The compounds described herein are useful in research relating to percutaneous penetration, i.e. the compounds of the present invention enhance percutaneous absorption of topically administered chemical agents, e.g. drugs, perfumes, dyes, insect repellants, etc. The compounds may be used to enhance percutaneous absorption of chemical agents at concentrations from about 1 to about 95 and preferably about 5 to about 25 percent by weight of a topical composition containing the chemical agent.

The compounds covered by the general formula above may be prepared by heating two moles or a slight excess of γ-butyrolactone with a diaminoalkane for 10 to 24 hours at 170°–250° C to obtain the N-bis-azacyclopentan-2-onyl alkane. This method is outlined below:

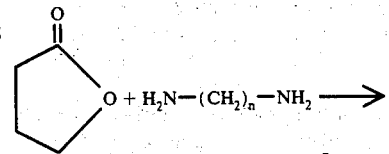

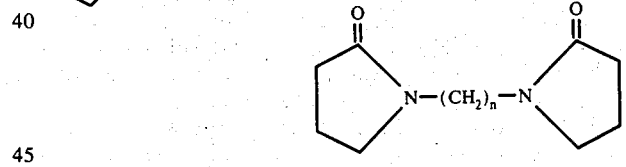

where n has the same meaning as before.

In an alternate method, azacyclopentan-2-one is treated with a dihaloalkane or an alkyldimesylate in the presence of a base. The preferred base is sodium hydride. The reaction is carried out under anhydrous condition in a hydrocarbon solvent, for example, dry toluene, at reflux temperature for a period of 20 to 72 hours in an inert atmosphere, for example, nitrogen. This method is outlined below:

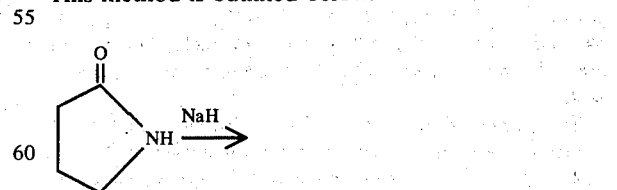

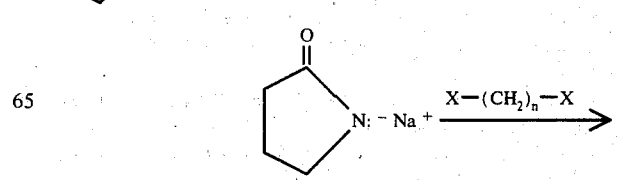

-continued

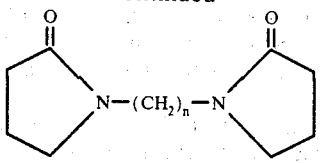

In the foregoing outline, X represents the halide or mesylate group.

In a second alternate method, the azacyclopentan-2-one may be treated with a haloalkanol in the presence of a base. The hydroxy group of the product may then be converted to a halide or a mesylate by known methods and treated under similar conditions as described above with another molecule or azacyclopentan-2-one to obtain the final product. The reaction involving the dihalo compound is preferred.

The process of this invention may find use with many physiologically active agents which are soluble in the vehicles disclosed.

Fungistatic and fungicidal agents such as, for example, thiabendazole, chloroxine, amphotericin, candicidin, fungimycin, nystatin, chlordantoin, clotrimazole, ethonam nitrate, miconazole nitrate, pyrrolnitrin, salicylic acid, fezatione, ticlatone, tolnaftate, triacetin and zinc and sodium pyrithione may be dissolved in the vehicles described herein and topically applied to affected areas of the skin. For example, fungistatic or fungicidal agents so applied are carried through the stratum corneum, and thereby successfully treat fungus-caused skin problems. These agents, thus applied, not only penetrate more quickly than when applied in the vehicles of the prior art, but additionally enter the animal tissue in higher concentrations and are retained for substantially longer time periods whereby a far more successful treatment is effected.

For example, the method of this invention may also be employed in the treatment of fungus infections on the skin caused by candida and dermatophytes which cause athletes foot or ringworm, by dissolving thiabendazole or similar antifungal agents in one of the vehicles and applying it to the affected area.

The invention is also useful in treating skin problems, such as for example, herpes simplex, which may be treated by a solution of iododeoxyuridine dissolved in one of the vehicles, or such problems as warts which may be treated with agents such as podophylline dissolved in one of the vehicles. Skin problems such as psoriasis may be treated by topical application of a solution of a conventional topical steroid in one of the vehicles or by treatment with theophylline or antagonists of β-adrenergic blockers such as isoproterenol in one of the vehicles. Scalp conditions such as alopecia areata may be treated more effectively by applying steroids such as triamcinolone acetonide dissolved in one of the vehicles of this invention directly to the scalp.

The present invention is also useful for treating mild eczema, for example, by applying a solution of fluocinolone acetonide or its derivatives; hydrocortisone, triamcinolone acetonide, indomethacin, or phenylbutazone dissolved in one of the vehicles to the affected area.

Examples of other physiologically active steroids which may be used with the vehicles include corticosteroids such as, for example, cortisone, cortodoxone, flucetonide, fludrocortisone, difluorsone diacetate, flurandrenolone acetonide, medrysone, amcinafel, amcinafide, betamethasone and its esters, chloroprednisone, clocortelone, descinolone, desonide dexamethasone, dichlorisone, difluprednate, fluchloronide, flumethasone, flunisolide, fluocinonide, flucortolone, fluoromethalone, fluperolone, fluprednisolone, meprednisone, methylmeprednisolone, paramethasone, prednisolone and prednisone.

This invention is also useful in antibacterial chemotherapy, e.g., in the treatment of skin conditions involving pathogenic bacteria. Typical antibacterial agents which may be used in this invention include sulfonomides, penicillins, cephalosporins, penicillinase, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, etc.

This invention is also useful in protecting ultra-sensitive skin or even normally sensitive skin from damage or discomfort due to sunburn. Thus, dermatitis actinica may be avoided by application of a sunscreen, such as para-aminobenzoic acid or its well-known derivatives dissolved in one of the vehicles, to skin surfaces that are to be exposed to the sun; and the protective para-aminobenzoic acid or its derivatives will be carried into the stratum corneum more successfully and will therefore be retained even when exposed to water or washing for a substantially longer period of time than when applied to the skin in conventional vehicles. This invention is particularly useful for ordinary suntan lotions used in activities involving swimming because the ultra-violet screening ingredients in the carriers of the prior art are washed off the skin when it is immersed in water.

This invention may also find use in treating scar tissue by applying agents which soften collagen, such as aminoproprionitrile or penicillamine dissolved in one of the vehicles of this invention topically to the scar tissue.

Agents normally applied as eye drops, ear drops, or nose drops are more effective when dissolved in the vehicles of this invention.

Agents used in diagnosis may be used more effectively when applied dissolved in one of the vehicles of this invention. Patch tests to diagnose allergies may be effected promptly without scratching the skin or covering the area subjected to an allergen when the allergens are applied in one of the vehicles of this invention.

This invention is also useful for topical application of cosmetic or esthetic agents. For example, compounds such as melanin-stimulating hormone (MSH) or dihydroxy acetone and the like are more effectively applied to skin to simulate a suntan when they are dissolved in one of the vehicles of this invention. The agent is carried into the skin more quickly and in greater quantity when applied in accordance with this invention. Hair dyes also penetrate more completely and effectively when dissolved in one of the vehicles of this invention.

The effectiveness of such topically applied materials as insect repellants or fragrances, such as perfumes and colognes, can be prolonged when such agents are applied dissolved in one of the vehicles of this invention.

It is to be emphasized that the foregoing are simply examples of physiologically active agents including therapeutic and cosmetic agents having known effects for known conditions, which may be used more effectively for their known properties in accordance with this invention.

In addition, the vehicles of the present invention may also be used to produce therapeutic effects which were not previously known. That is, by use of the vehicles described herein, therapeutic effects heretofore not known can be achieved.

As an example of the foregoing, griseofulvin is known as the treatment of choice for fungus infections of the skin and nails. Heretofore, the manner of delivery of griseofulvin has been oral. However, it has long been known that oral treatment is not preferred because of side effects resulting from saturation of the entire body with griseofulvin and the fact that only the outer layers of affected skin need to be treated. Therefore, because fungal infections are generally infections of the skin and nails, it would be advantageous to utilize griseofulvin topically. However, despite a long-felt need for a topical griseofulvin, griseofulvin has been used orally to treat topical fungus conditions because there was not heretofore known any formulation which could be delivered topically which would cause sufficient retention of griseofulvin in the skin to be useful therapeutically.

However, it has now been discovered that griseofulvin, in a range of therapeutic concentrations between about 0.1% and about 10% may be used effectively topically if combined with one of the vehicles described herein.

As a further example, acne is the name commonly applied to any inflammatory disease of the sebaceous glands; also *acne vulgaris*. The microorganism typically responsible for the acne infection is *Corynebacterium acnes*. Various therapeutic methods for treating acne have been attempted including topical antibacterials, e.g. hexachlorophene, and systemic antibiotics such as tetracycline. While the systemic antibiotic treatment are known to be partially effective, the topical treatments are generally not effective.

It has long been known that systemic treatment of acne is not preferred because of side effects resulting from saturation of the entire body with antibiotics and the fact that only the affected skin need by treated. However, despite a long-felt need for a topical treatment for acne, antibiotics generally have been used only systemically to treat acne because there was not heretofore known an anti-bacterial formulation which could be used topically which would be effective therapeutically in the treatment of acne. However, it has now been discovered that antibiotics, especially those of the lincomycin and erythryomycin families of antibiotics, may be used in the treatment of acne topically if combined with one of the vehicles described herein.

The antibiotics composition so applied is carried into and through the epidermis and deeper layers of the skin as well as into follicles and comedones (sebum-plugged follicles which contain *C. acnes*) in therapeutically effective amounts and thereby successfully may be used to temporarily eliminate the signs and symptoms of acne.

The term "physiologically active agent" is used herein to refer to a broad class of useful chemical and therapeutic agents including physiologically active steroids, antibiotics, antifungal agents, antibacterial agents, antineoplastic agents, allergens, antihistamic agents, anti-inflammatory agents, ultraviolet screening agents, diagnostic agents, perfumes, insect repellants, hair dyes, etc.

Dosage forms for topical application may include solution nasal sprays, lotions, ointments, creams, gels suppositories, sprays, aerosols and the like. Typical inert carrier which make up the foregoing dosage forms include water, acetone, isopropyl alcohol, freons, ethyl alcohol, polyvinyl pyrrolidone, propylene glycol, fragrances, gel-producing materials, mineral oil, stearyl alcohol, stearic acid, spermaceti, sorbitan monooleate, "Polysorbates", "Tweens," sorbital, methylcellulose, etc.

The amount of the composition, and thus of the physiologically active agent therein, to be administered will obviously be an effective amount for the desired result expected therefrom. This, of course, will be ascertained by the ordinary skill of the practitioner. Due to enhanced activity which is achieved, the dosage of agent may often be decreased from that generally applicable. In accordance with the usual prudent formulating practices, a dosage near the lower end of the useful range of the particular agent may be employed initially and the dosage increased as indicated from the observed response, as in the routine procedure of the physician.

The examples which follow illustrate the compositions of the present invention. Temperatures are given in degrees Centigrade.

EXAMPLE 1

Preparation of
N-bis-1,6-(azacyclopentan-2-onyl)-hexane 21.66 g (0.25M) of 1,6-diaminohexane and 11.62 g (0.1 mole) of γ-butyrolactone were heated overnight at 170°–180° C. The reaction mixture was cooled whereupon it solidified. Excess γ-butyrolactone was removed at reduced pressure and the hot liquid residue was poured into a crystallization dish where it immediately solidified. This was taken in chloroform and filtered to obtain 22.5 g (89%) of the product. (Alternatively, the excess γ-butyrolactone may be removed by washing with an organic solvent in which the product is insoluble instead of distilling it out at reduced pressure).

M.P. 100°–103°. NMR ($D_2O$) 1.3 – 2.8 δ complex; 3.3 – 4.1 δ complex.

EXAMPLE 2

Preparation of
N-bis-1,3-(azacyclopentan-2-onyl)-propane

A mixture of 11.0 g of 5% sodium hydride-mineral oil suspension and 105 ml of dry toluene (distilled over $CaH_2$) was stirred under nitrogen atmosphere as 20 g (0.235 mole) of azacyclopentane-2-one was added dropwise over a period of 7 hours. After the addition was complete, the mixture was refluxed for 1 hour and then 22.3 g (0.11 mole) of 1,3-dibromopropane was added dropwise over three hours. The refluxing was continued during the addition and for 72 hours thereafter. The mixture was cooled and filtered through celite. The solvent was removed to yield a residue consisting of two phases. The lower phase was removed and distilled at 170°–172°/0.01 mm. GC analysis showed a single peak and the N.M.R. spectrum was consistent with the expected product. This material was redistilled at 179°–180°/0.03 mm to yield 8.2 g of product.

G.C. one peak on 5% SE30 column. I.R. (liquid film): 3500, 2938, 2878, 1685, 1498, 1465, 1425, 1380, 1365, 1330, 1315(s), 1290, 1259, 1229, 1170, 1110, 1065, 998, 930, 852, 750, 735, 650 cms$^{-1}$.
N.M.R. (CDCl$_3$ + TMS) 1.5 – 2.7 δ; 3.2 – 3.9 δ.

EXAMPLE 3

The following solution formulation is prepared.

| | Solution (%) |
|---|---|
| Griseofulvin | 1 |
| N-bis-1,3-(azacyclopentan-2-onyl)-propane | 5 |
| Isopropyl myristate | 5 |
| Fragrance | 0.1 |
| Ethanol qs. ad | |

This formulation is effective in the treatment of fungus infections.

EXAMPLE 4

An aerosol form of the formulation of Example 3 is prepared by preparing the following mixture:

| | |
|---|---|
| Formulation | 25% |
| Freon[1] | 75% |

[1] Freon is 75/25 Freon 114/12.

EXAMPLE 5

The following cream formulation is prepared:

| | % |
|---|---|
| Clindamycin (base) | 1.0 |
| Stearyl alcohol, U.S.P. | 12.0 |
| Ethoxylated cholestrol | 0.4 |
| Synthetic spermaceti | 7.5 |
| Sorbitan monooleate | 1.0 |
| Polysorbate 80, U.S.P. | 3.0 |
| N-bis-1,3-(azacyclopentan-2-onyl)-propane | 10.0 |
| Sorbitol solution, U.S.P. | 5.5 |
| Sodium citrate | 0.5 |
| Chemoderm No. 844 Fragrance | 0.2 |
| Purified water qs. ad | |

This formulation is effective in the treatment of acne.

EXAMPLE 6

The following solution formulations are prepared:

| | A(%) | B(%) |
|---|---|---|
| Clindamycin base | — | 1.0 |
| Clindamycin phosphate acid | 1.3 | — |
| Sodium hydroxide | 0.077 | — |
| 1.0 Molar hydrochloric acid | — | 2.27 |
| Disodium edetate.2H$_2$O | 0.0033 | 0.0033 |
| Fragrances | 0.5 | 0.5 |
| N-bis-1,6-(azacyclopentan-2-onyl)-hexane | 15.0 | 15.0 |
| Purified water | 20.0 | 17.73 |
| Isopropanol qs. ad. | | |

These solutions are effective for the treatment of acne in humans.

EXAMPLE 7

The following solution formulation is prepared:

| | % |
|---|---|
| Neomycin sulfate | 0.5 |
| Lidocaine | 0.5 |
| Hydrocortisone | 0.25 |

| | % |
|---|---|
| N-bis-1,4-(azacyclopentan-2-onyl)-butane | 25.0 |
| Propylene glycol qs. ad. | |

This solution is effective for the treatment of otitis in domestic animals.

EXAMPLE 8

The following sunscreen emulsion is prepared:

| | % |
|---|---|
| p-amino benzoic acid | 2.0 |
| Benzyl alcohol | 0.5 |
| N-bis-1,5-(azacyclopentan-2-onyl)-pentane | 40.0 |
| Polyethylene glycol 400-MS | 10.0 |
| Isopropyl lanolate | 3.0 |
| Lantrol | 1.0 |
| Acetylated lanolin | 0.5 |
| Isopropyl myristate | 5.0 |
| Light mineral oil | 8.0 |
| Cetyl alcohol | 1.0 |
| Veegum | 1.0 |
| Propylene glycol | 3.0 |
| Purified water qs. ad | |

EXAMPLE 9

The following antineoplastic solution is prepared:

| | % |
|---|---|
| 5-Fluorouracil | 5 |
| N-bis-1,3-(azacyclopentan-2-onyl)-propane | 20 |
| Polyethylene glycol | 5 |
| Purified water qs. ad | |

EXAMPLE 10

The following insect repellant atomizing spray is prepared:

| | % |
|---|---|
| Diethyltoluamide | 0.1 |
| N-bis-1,3-(azacyclopentan-2-onyl)-propane | 10 |
| Ethanol qs. ad | |

EXAMPLE 11

The following lotion formulation may be prepared containing about 0.001 to 1 percent, with preferably 0.1 percent fluocinolone acetonide:

| | % |
|---|---|
| Fluocinolone acetonide | 0.001 – 1 |
| Cetyl alcohol | 15 |
| Propylene glycol | 10 |
| Sodium lauryl sulfate | 15 |
| N-bis-1,3-(azacyclopantan-2-onyl)-propane | 20 |
| Water qs. ad. | |

The steroid is dissolved in the vehicle and added to a stirred, cooling melt of the other ingredients. The preparation is particularly useful for the treatment of inflammed dermatoses by topical application to the affected skin area. The amount and frequency of application is in accordance with standard practice for topical application of this steroid. Penetration of the steroid into the inflammed tissue is enhanced and a therapeutic level is achieved more rapidly and sustained for longer duration than when the steroid is applied in conventional formulations.

EXAMPLE 12

The percutaneous penetration of one of the claimed vehicles was compared to a structurally related prior art vehicle by means of a diffusion cell using excised hairless mouse skin as a membrane. Skin specimens were obtained from male mice 14–16 weeks. Old test solution contained 2% 8-Bromo-cyclic-adenosine monophosphate and 1-% phosphate buffer (0.1M; pH 6.2) and equimolar amounts of vehicle. The volume of test solution applied to the membrane was 0.5 Ml/cm². The results represent average values obtained from 2–4 skin cells and are shown in Table 1 below.

Table 1

| Composition | Penetration (hrs) 25 | 50 | 75 | Flux (mole/cm²/min) | P.C[3] (μcm/min) | P.R[4] |
|---|---|---|---|---|---|---|
| A[1] | 5 | 50 | 100 | 0.033 | 1.346 | moderate |
| B[2] | 10 | 65 | 120 | 0.037 | 1.510 | moderate |

[1]A: 40% 1-methyl-azacyclopentan-2-one in propylene glycol
[2]B: Equimolar amounts of N-bis-1,3-azacyclopentan-2-onyl)-propane in propylene glycol.
[3]PC: Permeability Constant.
[4]PR: Penetration Rating

I claim:
1. A method for enhancing the penetration of physiologically active agents through human and animal body skin and membranes comprising administering to a human or animal a composition comprising an effective amount of said agent and a non-toxic, effective membrane penetrating amount of a compound having the formula

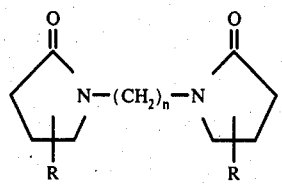

wherein R is selected from the group consisting of H and alkyl having 1–4 carbon atoms and $n$ is a positive integer from 1–18.

2. The method of claim 1 wherein the physiologically active agent is an antibacterial agent.

3. The method of claim 2, wherein the antibacterial agent is an antibiotic.

4. The method of claim 3 wherein the antibiotic is selected from the group consisting of lincomycin, clindamycin, erythromycin and pharmaceutically useful salts thereof.

5. The method of claim 1 wherein the physiologically active agent is a physiologically active steroid.

6. The method of claim 1 wherein the physiologically active agent is an antifungal agent.

7. The method of claim 1 wherein the physiologically active agent is iododeoxyuridine.

8. The method of claim 1 wherein the physiologically active agent is a sunscreen.

9. The method of claim 8 wherein the sunscreen is para-aminobenzoic acid or an active derivative thereof.

10. The method of claim 1 wherein the physiologically active agent is 5-fluorouracil.

11. The method of claim 1 wherein the physiologically active agent is an allergen.

* * * * *